United States Patent [19]

O'Lenick, Jr.

[11] Patent Number: 5,292,847

[45] Date of Patent: Mar. 8, 1994

[54] NOVEL SILICONE ALKOXYLATES

[75] Inventor: Anthony J. O'Lenick, Jr., Lilburn, Ga.

[73] Assignee: Siltech Corporation, Toronto, Canada

[21] Appl. No.: 128,161

[22] Filed: Sep. 29, 1993

Related U.S. Application Data

[63] Continuation-in-part of Ser. No. 37,655, Mar. 18, 1993, abandoned.

[51] Int. Cl.$^5$ .............................................. C08G 77/14
[52] U.S. Cl. ...................................... 528/14; 528/23; 528/27; 528/41; 556/439; 525/474
[58] Field of Search ................. 528/27, 41, 23, 14; 556/439; 525/474

[56] References Cited

U.S. PATENT DOCUMENTS 4,844,888 7/1989 Zawadzki .

OTHER PUBLICATIONS

Siltech, Inc. Silicone Fluids, Emulsions Antifoams and Specialties, 1989 and 1993.

*Primary Examiner*—Melvyn I. Marquis

[57] ABSTRACT

The invention relates to a series of novel silicone alkoxylates a process for their preparation and the application of these materials as emulsifiers for a variety of oil phases. This class of compounds are prepared by the reaction of a carboxy functional silicone and a ethylene oxide, propylene oxide or mixtures thereof. The products provide unique surfactant properties, specifically emulsification properties for many oil phases.

The compounds are useful for preparation of ultra mild products for use personal care applications for skin, hair care and related applications.

18 Claims, No Drawings

SILICONE ALKOXYLATES

BACKGROUND OF THE INVENTION

This application is a continuation in part of co-pending application Ser. No. 08/037,655 filed Mar. 18, 1993, now abandoned.

FIELD OF THE INVENTION

The invention relates to a series of novel silicone alkoxylates a process for their preparation and the application of these materials as emulsifiers for a variety of oil phases. This class of compounds are prepared by the reaction of a carboxy functional silicone and a ethylene oxide, propylene oxide or mixtures thereof. The products provide unique surfactant properties, specifically emulsification properties for many oil phases.

The compounds are useful for preparation of ultra mild products for use personal care applications for skin, hair care and related applications.

ARTS AND PRACTICES

Silicone compounds have been known to be active at the surface of cellulosic and synthetic fibers as well as paper.

They are good nondurable lubricants and are very stable to oxidation, however, their high cost and lack of efficiency at low concentrations as well as low durability have made their acceptance in commercial products quite low.

Many oil phases, which are insoluble in water, are emulsified to provide milky white opaque liquids which are easily formulated into a variety of applications. One problem here is that in order to obtain the necessary emulsion stability, relatively high loadings of traditional fatty surfactants are added. This minimizes the amount of oil phase delivered to the hair and skin and affects the feel on the skin and hair.

Carboxy functional silicone compounds useful as raw materials in the practice of the present invention are known to those skilled in the art. U.S. Pat. No. 4,844,888 issued in 1989 to Zawadizki discloses the carboxy functional silicone compounds useful as raw materials in the preparation of the compounds of the present invention.

OBJECT OF THE INVENTION

It is the object of the present invention to provide novel silicone alkoxylates. These compounds have unique surface active properties. The compounds of the present invention in addition to their surfactant properties, provide lubricity, and hydrophobicity when applied to hair and skin.

It is another objective of the current invention to provide a novel process for the preparation of silicone alkoxylates. It is still another objective of the invention to provide silicone alkoxylates which can be used in personal care, textile, and industrial formulations to render surfactant properties to personal care formulations.

SUMMARY OF THE INVENTION

The present invention relates to novel silicone alkoxylates. These compounds by virtue of the amide group are soluble in fatty and hydrocarbon products, but have many of the functional softening and lubrication properties of silicone. These materials are excellent additives for highly effective surface modifying finishes for fiber and textiles. The compounds of the present invention are substantive to cellulosic and synthetic fibers as well as metal surfaces and plastic polymers.

As will become clear from the disclosure, the compounds of the present invention while having silicone present in the molecule, have unique surfactant properties which can be tailored for specific applications. This property is a direct result of the structure.

HLB, the so called Hydrophylic-Liphophyllic Balance, is the ratio of oil soluble and water soluble portions of a molecule. The system was originally developed for ethoxylated products. Listed below are some approximations for the HLB value for surfactants as a function of their solubility in water.

| Solubility in Water | HLB Value | Description |
| --- | --- | --- |
| Insoluble | 4–5 | water in oil |
| Poorly dispersible (milky appearance) | 6–9 | wetting Agent |
| Translucent to clear | 10–12 | detergent |
| Very soluble | 13–18 | oil in water |

In order to obtain a product with surface activity, it is necessary to have a hydrophobic and hydrophylic portion within the molecule. The hydrophobe or oil soluble portion of the molecule in the compounds of the present invention is derived from a carboxy functional silicone. The hydrophyllic or water loving portion of the molecule is provided by the alkylene oxide.. namely ethylene oxide., propylene oxide or mixtures thereof. Butylene oxide and related alkoxylates are also useful in the preparation of compounds of the present invention.

When a surface active agent is added to water the molecules orientate themselves at the air water interface to minimize the free energy of the system. This means that the silicone portion of the molecule will be orientated into the air and the water soluble portion will be in solution. The surface tension will decrease as the concentration of surfactant molecules at the surface increases. At some concentration of surfactant, the ability to continue to reduce the surface tension by addition of more surfactant will stop. At that point micelles are formed. Continued addition of surfactant will not reduce surface tension. The concentration at which minimum surface tension is first reached is called the CMC (critical micelle concentration).

The minimum free energy of the system is obtained when the surfactant is at the air water interface. This surface orientation results in a decrease of surface tension. If oil or silicone is added to the system in which micelles were present the minimum energy state would be for the oil to be inside the micelle. The removal of oil from a substrate into a micelle is a phenomenon called detergency. If the micelle is small enough a to give a clear liquid a solution will be obtained. As the micelle swells an emulsion results. Emulsions are not clear and may range from slightly turbid to milk like. In an oil in water emulsion the water is the continuous phase. In a water in oil emulsion oil is the continuous phase.

Wetting is a property that is most directly affected by the surfactants at the interface, while detergent properties are generally micellar properties. While the relationship between surfactant molecules in micelles and those at the surface are in a dynamic equilibrium.. the time needed to establish the equilibrium is longer than might be immediately evident.

Surface active silicone compounds perform a variety of functions which include, (a) surface tension reduction, (b) wetting and detergency, (c) micelle formation, (d) emulsifying (f) solubilization, (g) foaming and (g) foam stabilization. The silicone nature of the surfactant introduces three clear advantages, (1) the silicone surfactant is itself substantive, conditioning and provides gloss to the hair and skin, (2) the silicone emulsifier is ultra mild to the skin and eyes and finally, (3) the emulsion prepared with these unique emulsifiers deliver their oil phase completely and easily upon application to skin and hair. This attribute results in the ability to use very low levels of emulsifier to obtain maximum benefit from the oil phase chosen.

The compounds of the present invention conform to the following structure:

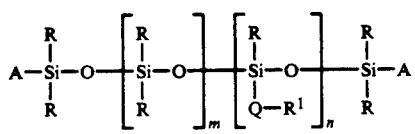

Wherein
R is methyl;
$R^1$ is —(—$CH_2$—$CH_2$—O—)x—($CH_2$—$CH(CH_3)CH_2$—O)y—($CH_2$—$CH_2$—O)z—H
Q is a —($CH_2$)c—C(O)—O—;
c is an integer ranging from 3 to 17;
A is either —R or —Q—$R^1$,
m is an integer ranging from 1 to 200;
n is an integer ranging 0 to 10 when A is —Q—$R^1$, and an integer ranging from 1 to 10 when A is R;
x, y and z are each independently integers ranging from 0 to 20 with the proviso that x+y+z be greater than or equal to 1.

The compounds of the present invention are prepared by the reaction of a carboxy functional silicone with an alkylene oxide selected from the group consisting of ethylene oxide propylene oxide or mixtures thereof.

The process used for the preparation of the compounds of the present invention comprises the alkoxylation reaction of (a) a carboxy containing silicone compound conforming to the following structure;

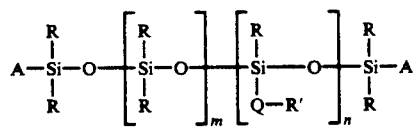

Wherein
R is methyl;
R' is —H;
Q is ($CH_2$)c—C(O)—O—;
c is an integer from 3 to 17;
A is selected from the group consisting of methyl and —Q—R';
m is an integer ranging from 1 to 200;
n is an integer ranging 0 to 10 when A is —Q—$R^1$. and an integer ranging from 1 to 10 when A is R: with (b) an alkylene oxide selected from the group consisting of ethylene oxide, propylene oxide and mixtures thereof; and (c) a catalyst selected from the group consisting of KOH, NaOH, $NaOCH_3$ and $H_3PO_4$;
said reaction to be carried out by reacting said carboxy functional silicone and said alkylene oxide in the presence of said catalyst.

The alkoxylation reaction is carried out by reacting the carboxy functional silicone and alkylene oxide with a suitable catalyst. Catalysts of interest for the preparation of these materials are alkaline catalysts like KOH, NaOH and the like, or acid catalysts like phosphoric acid.

PREFERRED EMBODIMENTS

In a preferred embodiment, x+y+z is greater than or equal to 3.
In a still more preferred, x+y+z is greater than 6.
In a preferred embodiment, x and z are zero.
In a preferred embodiment, y is zero.

EXAMPLES

The compounds of the present invention are prepared by the reaction of a carboxy functional silicone compound and an alkylene oxide selected from the group consisting of ethylene oxide, propylene oxide and mixtures thereof. Examples of suitable reactants are as follows;

REACTANTS

Carboxy Functional Silicone Compounds

Many manufacturers offer a series of carboxy functional silicone compounds suitable for use as raw materials in the preparation of the esters of the present invention. These materials are marketed under the many trade names. Siltech Inc, and Dow Corning.

The preferred method of placing this type of reactive carboxy group into the silicone polymer is by the reaction of silanic hydrogen containing polymer with a terminal unsaturated carboxylate. This technology is well known to those skilled in the art.

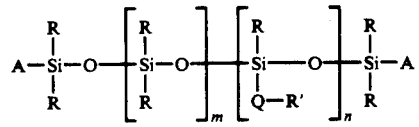

Wherein
R is methyl;
R' is —H;
Q is ($CH_2$)c—C(O)—O—;
c is an integer from 3 to 17;
A is methyl;
m is an integer ranging from 1 to 200;
n is an integer ranging 0 to 10 when A is —Q—$R^1$, and an integer ranging from 1 to 10 when A is R;

| Example | Name | c | n | m |
|---|---|---|---|---|
| 1 | Siltech C 1000 | 10 | 3 | 15 |
| 2 | Siltech C 1100 | 10 | 1 | 20 |
| 3 | Siltech C 1200 | 3 | 4 | 50 |
| 4 | Siltech C 1300 | 3 | 2 | 200 |
| 5 | Siltech C 1400 | 4 | 1 | 29 |
| 6 | Siltech C 1500 | 17 | 3 | 1 |
| 7 | Siltech C 1600 | 17 | 4 | 150 |
| 8 | Siltech C 1700 | 4 | 10 | 55 |

Terminal Substituted Carboxy Functional Silicone

Terminal substituted carboxy functional silicone compounds are well known and are marketed in the trade under many names.

The preferred method of placing this type of carboxyl group into the silicone polymer is by the reaction of terminal silanic hydrogen containing polymer with a terminal vinyl containing carboxy compound.

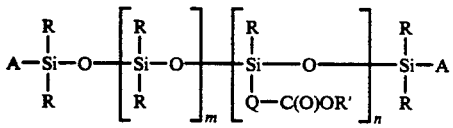

Wherein
R is methyl;
R' is —H;
Q is $(CH_2)_c$—C(O)—O—;
c is an integer from 3 to 17;
n is 0
A is —Q—R';

| Example | Name | c | m |
|---------|------------|----|-----|
| 9 | Siltech CT 701 | 10 | 1 |
| 10 | Siltech CT 706 | 3 | 200 |
| 11 | Siltech CT 710 | 17 | 50 |
| 12 | Siltech CT 750 | 10 | 100 |
| 13 | Siltech CT 790 | 3 | 150 |

General Reaction Conditions

The alkoxylation vessel useful for the preparation of the compounds are well known to those skilled in the art and are available for example from Parr Inc.

The exact conditions used for alkoxylation can be varied over a relatively wide range. These conditions are typical;
1. To a clean, dry alkoxylation vessel having the ability to heat the contents to 200 C. and having the ability to accommodate pressures of up th 100 psi, add the carboxy functional silicone.
2. Add the specified amount of the specified catalyst under good agitation.
3. If ethylene oxide is to be added first, add the ethylene oxide, at between 260-290 F. and 45 psig.
4. After all the ethylene oxide has been added, hold for one hour. Apply vacuum strip to remove any residual low levels of ethylene oxide.
5. If propylene oxide is being added propoxylate at 290-300F. and 45 psig.
6. After all the propylene oxide has been added, hold for one hour. Apply vacuum strip to remove any residual low levels of propylene oxide.
7. If ethylene oxide is to be added again, add all the ethylene oxide, at between 260-290 F. and 45 psig.
8. After all the ethylene oxide has been added, hold for one hour. Apply vacuum strip to remove any residual low levels of ethylene oxide.

The process can be alternated using any amount of ethylene oxide, propylene oxide or mixtures thereof.

EXAMPLE 14

The product is prepared according to the following procedure;
1. To a clean, dry alkoxylation vessel having the ability to heat the contents to 200 C. and having the ability to accommodate pressures of up th 100 psi, add 609.0 grams of Siltech C-1000.
2. Add the 0.1% by weight (based upon the total weight of product to be produced) KOH powder under good agitation. In this case 0.1% of 3.440.0 grams or 34.4 grams)
3. Add 880 grams of ethylene oxide at between 260-290 F. and 45 psig.
4. After all the ethylene oxide has been added, hold for one hour. Apply vacuum strip to remove any residual low levels of ethylene oxide.
5. Add 1180.0 grams of propylene oxide at 290-300 F. and 45 psig.
6. After all the propylene oxide has been added, hold for one hour. Apply vacuum strip to remove any residual low levels of propylene oxide.
7. Add the last 880 grams of ethylene oxide at between 260-290 F. and 45 psig.
8. After all the ethylene oxide has been added, hold for one hour. Apply vacuum strip to remove any residual low levels of ethylene oxide.

The product is used without additional purification.

EXAMPLE 15-52

Example 14 is repeated, only this time the specified amount of the specified carboxy functional silicone is used in place of Siltech C-1 000. The specified amount and type of catalyst is used in place of the specified amount of KOH and the specified amounts of oxide are used in place of the amounts of ethylene oxide (EO 1), propylene oxide (PO) and ethylene oxide (EO 2) specified.

| | Catalysts Types | | |
|---|---|---|---|
| A | Sodium Methoxide (NaOCH$_3$) | 0.2% of total batch weight | |
| B | Sodium Methoxide (NaOCH$_3$) | 0.1% of total batch weight | |
| C | Sodium Hydroxide (NaOH) | 0.2% of total batch weight | |
| D | Sodium Hydroxide (NaOH) | 0.1% of total batch weight | |
| E | Phosphoric Acid (H$_3$PO$_4$) | 0.2% of total batch weight | |

| Example Number | Carboxy Silicone Example/grams | Catalyst System | EO 1 grams | PO grams | EO 2 grams |
|---|---|---|---|---|---|
| 15 | 2 1827.0 | A | 0 | 44 | 0 |
| 16 | 3 1051.0 | A | 0 | 59 | 220 |
| 17 | 4 7570.0 | A | 0 | 120 | 880 |
| 18 | 5 2409.0 | A | 0 | 180 | 400 |
| 19 | 8 361.0 | A | 0 | 236 | 220 |
| 20 | 7 3100.0 | A | 0 | 1180 | 880 |
| 21 | 8 524.2 | A | 0 | 500 | 500 |
| 22 | 9 290.0 | A | 0 | 50 | 50 |
| 23 | 10 7553.0 | A | 880 | 1180 | 880 |
| 24 | 11 2200.0 | A | 100 | 0 | 0 |
| 25 | 12 4000.0 | A | 25 | 0 | 0 |
| 26 | 13 5700.0 | A | 880 | 0 | 0 |
| 27 | 1 609.0 | A | 500 | 0 | 0 |
| 28 | 2 1827.0 | B | 5 | 0 | 0 |
| 29 | 3 1051.0 | B | 0 | 100 | 20 |
| 30 | 4 7570.0 | B | 500 | 500 | 500 |
| 31 | 5 2409.0 | B | 880 | 1180 | 200 |
| 32 | 6 361.0 | B | 120 | 10 | 200 |
| 33 | 7 3100.0 | B | 10 | 1 | 10 |
| 34 | 8 524.2 | B | 50 | 1000 | 50 |
| 35 | 9 290.0 | B | 500 | 10 | 800 |
| 36 | 10 7553.0 | B | 200 | 10 | 190 |
| 37 | 11 2200.0 | B | 100 | 45 | 0 |
| 38 | 12 4000.0 | B | 150 | 3 | 0 |
| 39 | 13 5700.0 | B | 25 | 45 | 45 |
| 40 | 1 609.0 | B | 35 | 1180 | 56 |
| 41 | 2 1827.0 | B | 23 | 0 | 0 |
| 42 | 3 1051.0 | C | 16 | 3 | 3 |
| 43 | 4 7570.0 | C | 12 | 54 | 0 |
| 44 | 5 2409.0 | C | 54 | 500 | 500 |
| 45 | 6 361.0 | C | 44 | 10 | 10 |
| 46 | 7 3100.0 | C | 59 | 5 | 5 |

| | | -continued | | | | |
|---|---|---|---|---|---|---|
| 47 | 8 | 524.2 | C | 800 | 0 | 0 |
| 48 | 9 | 290.0 | C | 450 | 300 | 300 |
| 49 | 10 | 7553.0 | D | 650 | 650 | 650 |
| 50 | 11 | 2200.0 | D | 98 | 1 | 10 |
| 51 | 12 | 4000.0 | A | 44 | 0 | 0 |
| 52 | 13 | 5700.0 | B | 0 | 59 | 0 |

EO 1 refers to the first addition of ethylene oxide.
PO refers to the addition of propylene oxide.
EO 2 refers to the second addition of ethylene oxide.

Therefore $R^1$ is:

$$-(CH_2-CH_2-O)_x-(CH_2-CH(CH_3O)_y-(CH_2-CH_2-O)_z-H;$$
$$\text{EO 1} \quad\quad\quad \text{PO} \quad\quad\quad \text{EO 2}$$

Surfactant Properties
Typical Emulsions

The compounds of the present invention are good emulsifiers for a variety of oil phases. A typical test formulation is as follows:

| Ingredient | % by weight |
|---|---|
| Emulsifier | 5.0 |
| Oil Phase | 45.0 |
| Water | 50.0 |

| Oil Phase | Example |
|---|---|
| Lanolin | 51 |
| Mineral spirits | 47 |
| Beeswax | 48 |
| Pine oil | 19 |
| Silicone Oil | 35 |
| Castor oil | 22 |
| Petrolatum | 44 |

As illustrated above the compounds of the present invention can be tailored to allow for the emulsion of specific oil phases. This flexibility, the ability of the emulsifier to be incorporated into the emulsion at low concentrations and the fact that the silicone emulsifier has no affect upon skin feel are all very desirable attributes of the compounds of the present invention. They are unexpected advantages over the commonly used surfactants.

What is claimed:

1. A silicone compound which conforms to the following structure;

$$A-\underset{\underset{R}{|}}{\overset{\overset{R}{|}}{Si}}-O-\left[\underset{\underset{R}{|}}{\overset{\overset{R}{|}}{Si}}-O\right]_m\left[\underset{\underset{Q-R^1}{|}}{\overset{\overset{R}{|}}{Si}}-O\right]_n\underset{\underset{R}{|}}{\overset{\overset{R}{|}}{Si}}-A$$

wherein
R is methyl;
$R^1$ is $-(-CH_2-CH_2-O-)_x-(CH_2-CH(CH_3)CH_2-O)_y-(CH_2-CH_2-O)_z-H$
Q is a $-(CH_2)_c-CO(O)-O-$;
c is an integer ranging from 3 to 17;
A is either $-R$ or $-Q-R^1$,
m is an integer ranging from 1 to 200;
n is an integer ranging 0 to 10 when A is $-Q-R^1$, and an integer ranging from 1 to 10 when A is R;
x, y and z are each independently integers ranging from 0 to 20 with the proviso that $x+y+z$ be greater than or equal to 1.

2. A silicone compound of claim 1 wherein $x+y+z$ is greater than or equal to 3.
3. A silicone compound of claim 1 wherein $x+y+z$ is greater than or equal to 6.
4. A silicone compound of claim 1 wherein x and z are each zero.
5. A silicone compound of claim 1 wherein y is zero.
6. A silicone compound of claim 1 wherein c is 10.
7. A silicone compound of claim 6 wherein $x+y+z$ is greater than or equal to 3.
8. A silicone compound of claim 6 wherein x and z are each zero.
9. A silicone compound of claim 6 wherein y is zero.
10. A silicone compound prepared by reacting
   (a) a carboxy containing silicone compound conforming to the following structure;

$$A-\underset{\underset{R}{|}}{\overset{\overset{R}{|}}{Si}}-O-\left[\underset{\underset{R}{|}}{\overset{\overset{R}{|}}{Si}}-O\right]_m\left[\underset{\underset{Q-R'}{|}}{\overset{\overset{R}{|}}{Si}}-O\right]_n\underset{\underset{R}{|}}{\overset{\overset{R}{|}}{Si}}-A$$

Wherein
R is methyl;
R' is $-H$;
Q is $(CH_2)_c-C(O)-O-$;
c is an integer from 3 to 17;
A is selected from the group consisting of methyl and $-Q-R'$;
m is an integer ranging from 1 to 200;
n is an integer ranging 0 to 10 when A is $-Q-R^1$, and an integer ranging from 1 to 10 when A is R;
with
   (b) an alkylene oxide selected from the group consisting of ethylene oxide, propylene oxide and mixtures thereof; in the presence of
   (c) a catalyst selected from the group consisting of KOH, NaOH, NaOCH$_3$ and H$_3$PO$_4$.

11. A silicone compound of claim 10 wherein said catalyst is KOH.
12. A silicone compound of claim 10 wherein said catalyst is NaOH.
13. A silicone compound of claim 10 wherein said catalyst is NaOCH$_3$.
14. A silicone compound of claim 10 wherein said catalyst is H$_3$PO$_4$.
15. A silicone compound of claim 10 wherein c is 10.
16. A silicone compound of claim 10 wherein $x+y+z$ is greater than or equal to 3.
17. A silicone compound of claim 10 wherein x and z are each zero.
18. A silicone compound of claim 10 wherein y is zero.

* * * * *